US011629322B2

(12) United States Patent
Prabhudharwadkar et al.

(10) Patent No.: US 11,629,322 B2
(45) Date of Patent: Apr. 18, 2023

(54) IMPELLER INCLUDING ONE OR MORE TURBULATORS, FOR A BIOREACTOR SYSTEM

(71) Applicant: GLOBAL LIFE SCIENCES SOLUTIONS USA LLC, Marlborough, MA (US)

(72) Inventors: Deoras Prabhudharwadkar, Bangalore (IN); Ashok Gopinath, Bangalore (IN)

(73) Assignee: GLOBAL LIFE SCIENCES SOLUTIONS USA LLC, Marlborough, MA (US)

( * ) Notice: Subject to any disclaimer, the term of this patent is extended or adjusted under 35 U.S.C. 154(b) by 819 days.

(21) Appl. No.: 16/466,670

(22) PCT Filed: Dec. 4, 2017

(86) PCT No.: PCT/EP2017/081294
§ 371 (c)(1),
(2) Date: Jun. 5, 2019

(87) PCT Pub. No.: WO2018/104197
PCT Pub. Date: Jun. 14, 2018

(65) Prior Publication Data
US 2019/0345433 A1    Nov. 14, 2019

(30) Foreign Application Priority Data
Dec. 5, 2016   (IN) .............. 201641041425

(51) Int. Cl.
*C12M 1/06* (2006.01)
*B01F 23/233* (2022.01)
(Continued)

(52) U.S. Cl.
CPC ........... *C12M 27/02* (2013.01); *B01F 23/233* (2022.01); *B01F 27/0531* (2022.01);
(Continued)

(58) Field of Classification Search
CPC ... C12M 27/02; B01F 23/233; B01F 27/0531; B01F 27/1111; B01F 27/11251;
(Continued)

(56) References Cited

U.S. PATENT DOCUMENTS

| 2,010,094 A | 8/1935 | Leinweber |
| 2013/0189767 A1 | 7/2013 | Cheng et al. |
| 2018/0071698 A1* | 3/2018 | Multner ............... B01F 27/1125 |

FOREIGN PATENT DOCUMENTS

| CN | 105251394 | 1/2016 |
| CN | 105251394 A | 1/2016 |
(Continued)

OTHER PUBLICATIONS

Epo translation of JP 2014136203 (Year: 2014).*
(Continued)

*Primary Examiner* — Stephen Hobson
(74) *Attorney, Agent, or Firm* — Grogan, Tuccillo & Vanderleeden, LLP

(57) ABSTRACT

An impeller, for example, a Rushton impeller for a bioreactor system is disclosed. The impeller includes a hub, optionally including a slot, a plurality of blades, and one or more turbulators. The plurality of blades is disposed along a circumferential direction of the hub and spaced apart from each other. Each of the plurality of blades is coupled to at least a portion of a circumference and/or a top surface of the hub. Each blade of the plurality of blades includes a pressure face and a suction face. The one or more turbulators is disposed on at least a portion of the suction face, the pressure face, or both, of a blade of the plurality of blades.

17 Claims, 11 Drawing Sheets

(51) Int. Cl.
  *B01F 27/191*    (2022.01)
  *B01F 27/053*    (2022.01)
  *B01F 27/1111*   (2022.01)
  *B01F 27/1125*   (2022.01)
  *B01F 33/453*    (2022.01)
  *B01F 35/92*     (2022.01)
  *B01F 35/513*    (2022.01)
  *B01F 35/90*     (2022.01)
  *B01F 101/44*    (2022.01)

(52) U.S. Cl.
  CPC ..... *B01F 27/1111* (2022.01); *B01F 27/11251* (2022.01); *B01F 27/191* (2022.01); *B01F 33/4534* (2022.01); *B01F 35/513* (2022.01); *B01F 35/92* (2022.01); *B01F 23/23362* (2022.01); *B01F 2035/99* (2022.01); *B01F 2101/44* (2022.01)

(58) Field of Classification Search
  CPC .. B01F 27/191; B01F 33/4534; B01F 35/513; B01F 35/92; B01F 23/23362; B01F 2035/99; B01F 2101/44
  See application file for complete search history.

(56) References Cited

FOREIGN PATENT DOCUMENTS

| | | | |
|---|---|---|---|
| DE | 1782485 | A1 | 2/1972 |
| DE | 2544204 | A1 | 4/1977 |
| EP | 0403091 | A2 | 12/1990 |
| EP | 2836340 | | 2/2015 |
| GB | 223296 | A | 10/1924 |
| JP | 63-48499 | | 4/1988 |
| JP | S63-91075 | | 4/1988 |
| JP | 2007167708 | * | 7/2007 |
| JP | 2014136203 | * | 7/2014 |
| JP | 2014136203 | A | 7/2014 |
| SU | 1494955 | A1 | 7/1989 |

OTHER PUBLICATIONS

Epo translation of JP 2007167708 (Year: 2007).*
Japanese Office Action dated Sep. 13, 2021 issued in corresponding Japanese Patent Application No. 2019-530035.
Indian Examination Report dated Sep. 30, 2019 issued in corresponding Indian Patent Application No. 201641041425.

* cited by examiner

IMPELLER INCLUDING ONE OR MORE TURBULATORS, FOR A BIOREACTOR SYSTEM

CROSS REFERENCE TO RELATED APPLICATIONS

This application is a National Stage Patent Application of International Application No. PCT/EP2017/081294, filed on Dec. 4, 2017, which claims priority to Indian Patent Application No. 201641041425, filed on Dec. 5, 2016, both of which are incorporated by reference in their entireties.

BACKGROUND

The present disclosure relates generally to an impeller for bioreactor systems, and more particularly, to modifications provided on a blade of such impeller.

Cell culture technology has advanced significantly over the last few decades and has contributed in therapeutic applications, clinical studies, pharmaceutical research and development, and bioprocess industry. Bioreactor systems are generally used to culture cells. Typically, a bioreactor system is configured to receive and grow a plurality of cells, referred to as "starter cells", in a cell-culture media present in a culture vessel of the bioreactor system. The efficiency of the bioreactor system largely depends on one or more parameters such as a level of potential of hydrogen (pH), a level of dissolved oxygen (DO), and temperature of the cell-culture media.

During operation, the culture vessel is heated to provide a conducive temperature to grow the plurality of cells and prevent water condensation on side walls of the culture vessel. Further, air is injected into the culture vessel and stirred with the cell-culture media using an impeller to uniformly disperse the air in the cell-culture media and maintain desirable levels of pH and DO in the cell-culture media to promote cell growth. The impeller includes a plurality of blades. Typically, injection of air in the culture vessel produces air bubbles within the cell-culture media. The air bubbles tend to gather on corresponding suction faces of the plurality of blades of the impeller. Further, the air bubbles exhibit the tendency to coalesce with each other to form larger air bubbles. Generally, the larger air bubbles reduce an interfacial area (i.e., area density) between the air and cell-culture media. Reduced interfacial area in turn, adversely affects oxygen (i.e., air) transfer rate to the plurality of cells present in the cell-culture media, thereby affecting the cell growth and performance of the bioreactor system.

The impeller may be rotated at a higher speed to shear the large sized air bubbles and increase the area density between the air and cell-culture media. However, increased speed of the impeller may undesirably shear the plurality of cells.

BRIEF DESCRIPTION

In accordance with one embodiment, an impeller, for example, a Rushton impeller for a bioreactor system is disclosed. In accordance with aspects of the present technique, the impeller includes a hub, a plurality of blades, one or more turbulators and optionally a slot included in the hub. The plurality of blades is disposed along a circumferential direction of the hub and spaced apart from each other, where each of the plurality of blades is coupled to at least a portion of a circumference of the hub, and where each blade of the plurality of blades includes a pressure face and a suction face. The one or more turbulators is disposed on at least a portion of the suction face, the pressure face, or both, of a blade of the plurality of blades.

In accordance with another embodiment, a bioreactor sub-system is disclosed. In accordance with aspects of the present technique, the bioreactor sub-system includes a culture vessel and at least one impeller. The culture vessel is used for culturing a plurality of cells dispersed in a cell-culture media. The at least one impeller is disposed within the culture vessel and configured to stir the cell-culture media and the plurality of cells. The at least one impeller includes a hub, a plurality of blades, one or more turbulators and optionally a slot included in the hub. The plurality of blades is disposed along a circumferential direction of the hub and spaced apart from each other, where each of the plurality of blades is coupled to at least a portion of a circumference of the hub, and where each blade of the plurality of blades includes a pressure face and a suction face. The one or more turbulators is disposed on at least a portion of the suction face, the pressure face, or both, of a blade of the plurality of blades.

In accordance with yet another embodiment, a bioreactor system is disclosed. In accordance with aspects of the present technique, the bioreactor system includes a culture vessel, a heating assembly, an air introducing unit or sparger, and at least one impeller. The culture vessel is used for culturing a plurality of cells dispersed in a cell-culture media. The heating assembly is coupled to the culture vessel for heating the cell-culture media. The air introducing unit or sparger is operatively coupled to the culture vessel and configured to inject air or a gas into the culture vessel. The at least one impeller is disposed in the culture vessel and configured to stir the cell-culture media and the plurality of cells. The at least one impeller includes a hub, a plurality of blades, one or more turbulators and optionally a slot included in the hub. The plurality of blades is disposed along a circumferential direction of the hub and spaced apart from each other, where each of the plurality of blades is coupled to at least a portion of a circumference of the hub, and where each blade of the plurality of blades includes a pressure face and a suction face. The one or more turbulators is disposed on at least a portion of the suction face, the pressure face, or both, of a blade of the plurality of blades.

DRAWINGS

These and other features and aspects of embodiments of the present technique will become better understood when the following detailed description is read with reference to the accompanying drawings in which like characters represent like parts throughout the drawings, wherein.

DEFINITIONS

Figure 1:
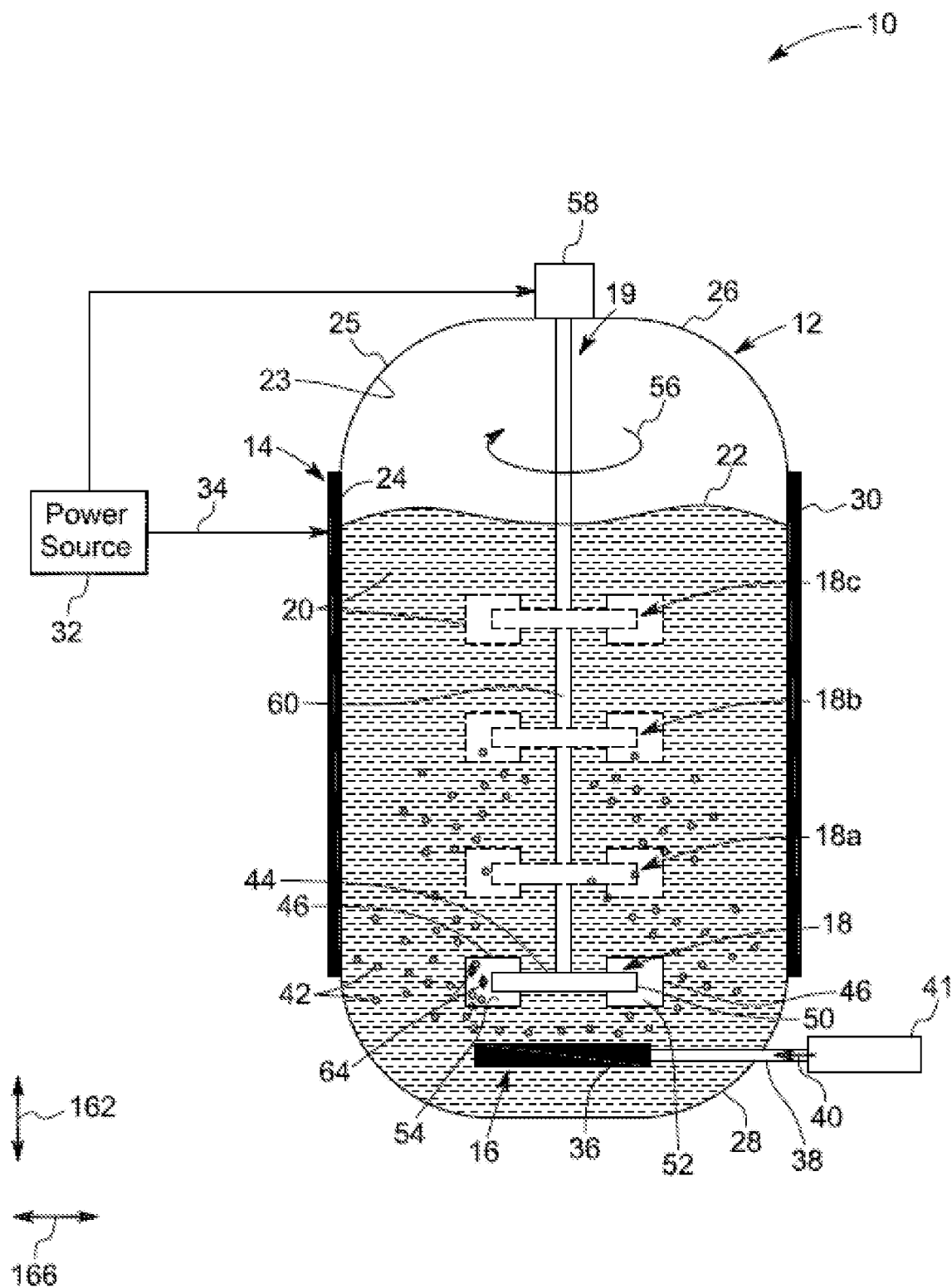
FIG. 1 is a schematic side view of a bioreactor system, in accordance with aspects of the present technique.

To more clearly and concisely describe and point out the subject matter of the claimed invention, the following definitions are provided for specific terms that are used in the following description and the claims appended hereto.

The singular forms "a" "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified.

Accordingly, unless indicated to the contrary, the numerical parameters set forth in the following specification and attached claims are approximations that may vary depending upon the desired properties sought to be obtained by the embodiments of the present invention. At the very least each numerical parameter should at least be construed in light of the number of reported significant digits and by applying ordinary rounding techniques.

As used herein to describe the present invention, directional terms such as "up", down", "top", "bottom", "vertical", "horizontal", as well as any other directional terms, refer to the directions as shown in the appended drawings. Those are also the directions of a reactor vessel or bioreactor as used in the normal operational position.

DETAILED DESCRIPTION

Embodiments discussed herein disclose an impeller, for example a Rushton impeller, for a bioreactor system, such as, but not limited to, a stirred-tank bioreactor system. In operation, air or a gas/gas mixture comprising oxygen is introduced in a cell culture vessel to promote cell growth of a plurality of cells present in a cell-culture media. In the following, the term "air" is used for a gas or gas mixture comprising oxygen, e.g. a nitrogen/oxygen mixture. Enhanced mixing of air with the cells results in enhanced performance of the bioreactor system. In some embodiments, the impeller includes one or more turbulators that are configured to generate turbulence proximate one side or face of one or more blades of the impeller to enhance mixing of the introduced air with the plurality of cells. This side may be referred to or defined as a suction face of the one or more blades. In certain embodiments, the turbulators are configured to generate eddies around the one face of the one or more blades. Generation of eddies, reduces or minimizes coalescing and/or sticking of air bubbles and promotes breaking of the air bubbles. Accordingly, the impeller of the present specification is configured to increase the interfacial area (i.e., area density) between the air and the cell-culture media. Consequently, the bioreactor system of the present specification is configured to increase the oxygen transfer rate for the cell growth of the plurality of cells present in the cell-culture media.

In some embodiments, the impeller includes a hub, a plurality of blades, and one or more turbulators. The plurality of blades is disposed along the circumference of the hub and spaced apart from each other along the circumferential direction of the hub. Each blade of the plurality of blades comprises a tip edge and a hub edge. Further, each of the plurality of blades is coupled to at least a portion of a circumference of the hub via at least a portion of the hub edge. Further, each blade of the plurality of blades includes a pressure face and a suction face, the pressure and suction faces are disposed between the tip and hub edges. Further, the pressure and suction faces form opposing faces of a blade of the plurality of blades. The one or more turbulators are disposed on one or more blades of the plurality of blades. Further, the turbulators are disposed on at least a portion of suction faces of the one or more blades of the plurality of blades.

In certain embodiments, a turbulator may include a physical feature that is present or disposed on at least a portion of a suction face of a blade. The physical feature of the turbulator is configured to generate eddies or turbulent eddies in the cell-culture media during operation of the bioreactor system. In some embodiments, non-limiting examples of turbulators may include a rib, a groove, a dimple, a through-opening, a protrusion, a corrugation, a corrugated surface, or combinations thereof. In some embodiments, the one or more turbulators may be disposed closer to a tip edge compared to the hub edge of the blade. In certain embodiments, the one or more turbulators may contribute to a non-planar nature of the suction face of the blade to prevent coalescing/sticking of the air bubbles to the suction face.

The pressure face of the blade experiences relatively higher pressure relative to the suction face. The suction face and pressure face of a blade are defined based on a direction of rotation of an impeller employing that blade. As used herein, the term "tip edge" refers to a foremost edge or side of the blade, which faces the cell-culture media during rotation of the impeller. Further, the term "hub edge" refers to an edge of the blade, which is disposed opposite to the tip edge and coupled to the hub of the impeller.

FIG. 1 is a schematic diagram of an embodiment of a bioreactor system 10 in accordance with one exemplary embodiment of the present technique. The bioreactor system 10, for example, a stirred-tank bioreactor system includes a culture vessel 12, a heating assembly 14, an air introducing unit or sparger 16, and at least one impeller 18.

In some embodiments, the bioreactor system 10 is used for culturing a plurality of cells 20. In one embodiment, the bioreactor system 10 is a batch processing system, which may be configured to culture a determined quantity of the plurality of cells 20 in a culture vessel 12. While in some other embodiments, the bioreactor system 10 may be a continuous processing system. Such a continuous processing bioreactor system 10 may include one or more conduits (not shown in FIG. 1) coupled to the culture vessel 12 to continuously add or remove the plurality of cells 20, a cell-culture media 22, nutrients, acid, base, or combinations thereof, in (or from) the culture vessel 12. In some embodiments, the one or more conduits may be pre-coupled to the culture vessel 12 and may be sterilized prior to commencing operation of the system 10.

The culture vessel 12 is a biocompatible container configured to receive and store the plurality of cells 20 and the cell-culture media 22 and provide a conducive environment for growth of the plurality of cells 20 in the culture vessel 12. In the illustrated embodiment, the culture vessel 12 has a cylindrical structure and includes a side wall 24, a top portion 26, and a bottom portion 28. The top portion 26 and the bottom portion 28 are coupled to the side wall 24. In some embodiments, the side wall 24, the top portion 26, and the bottom portion 28 may or may not be physically separate portions of the culture vessel 12. Although not illustrated, the culture vessel 12 may have shapes other than a cylindrical shape, by way of example, in some embodiments, the culture vessel 12 may have a conical structure or a flower-shaped structure depending on the application and design criteria. The culture vessel 12 has a volume capacity in a range from about 20 milliliters to 2 $m^3$, such as from about 20 milliliters to about 10 liters or from about 10 liters to about 2 $m^3$, and may be configured to maintain a specific heat transfer area and a specific gas transfer area for the growth of the plurality of cells 20. Further, the culture vessel 12 may be designed to accommodate significant changes in cell-culture media 22 volume without affecting bioreactor dynamics. The term "bioreactor dynamics" refers to a rate of change of internal parameters of the bioreactor system 100 with respect to a change in external parameters of the bioreactor system 10. In certain embodiments, the internal parameters of the bioreactor system 10 include the pH, the concentration of dissolved oxygen (DO), temperature, mixing/agitating speed, and time constants. Non-limiting examples of the external parameters may include ambient temperature, volume of the cell-culture media, quantity of air, and flow rate of air.

In certain embodiments, the bioreactor system 10 may additionally include a bag or a flexible container disposed inside the culture vessel 12. In such an embodiment, the bag or flexible container may line the interior of the culture vessel 12 and is configured to receive the plurality of cells 20 and the cell-culture media 22. In one embodiment, the bag or flexible container is pre-filled with the plurality of cells 20 (i.e., cell-inoculum) and then may be placed within the culture vessel 12 followed by addition of cell-culture media 22 to the bag. In some embodiments, the bag may be a disposable culture bag, such as culture bags from Wave™ or Xcellerex® (GE Healthcare Bio-Sciences, Marlborough, Mass.). In such embodiments, the bag or flexible container may help maintain sterility of the culture vessel 12. In certain embodiments, the bioreactor system 10 may further include a biocompatible coating (not shown in FIG. 1), such as a biomolecular coating disposed along an inner surface 23 of the culture vessel 12. In some embodiments, the biomolecular coating may be comprised of biologically derived proteins or peptides, recombinant proteins or synthetic peptides or growth factors that activate, promote proliferation or differentiation of specific cell populations.

In certain embodiments, the culture vessel 12 is made of glass, polymer, ceramic, metal, or combination thereof. In some embodiments, the culture vessel 12 is made of metal such as aluminum, copper, and the like. In certain embodiments, the culture vessel 12 is made of heat conducting non-metallic material. In some embodiments, the culture vessel 12 of the bioreactor is made of thermoplastic. In some embodiments, the culture vessel 12 is made of a biodegradable material. In some of these embodiments, the culture vessel 12 may be a disposable single use culture vessel. In such embodiments, culture vessel 12 may be a flexible bag, e.g. manufactured from one or more sheets of flexible plastic film or flexible plastic laminate. In some other embodiments, the culture vessel 12 is a multiple use vessel, e.g. made of a durable and rigid material, for example, but not limited to, glass, polymer, or metal. In certain embodiments, the culture vessel 12 is manufactured using additive manufacturing (for example, three-dimensional (3D) printing technique), a molding technique, machining, die casting, and the like.

The heating assembly 14 is coupled to the culture vessel 12 for heating the cell-culture media 22 via the culture vessel 12. In some embodiments, the heating assembly 14 includes a heating component 30 and a power source 32 coupled to the heating component 30 via a wired or wireless connection. In the illustrated embodiment, the power source 32 is coupled to the heating component 30 using a power cable 34. In the illustrated embodiment, the heating component 30 is coupled to the side wall 24 of the culture vessel 12. Specifically, the heating component 30 is disposed along an outer surface 25 of the side wall 24 of the culture vessel 12. Additionally, or alternatively, the heating component 30 may be coupled to the top portion 26 and/or the bottom portion 28 of the culture vessel 12 depending on the application and design criteria. In certain embodiments, the heating component 30 conforms to the shape of the culture vessel 12. In certain embodiments, the heating component 30 may be coupled to the culture vessel 12 via a suitable mechanism such as an adhesive. The power source 32 is configured to supply an electrical power to the heating component 30 to heat the culture vessel 12 and thereby heat the cell-culture media 22. Non-limiting examples of the heating component 30 may include a non-contact heater such as an infrared (IR) heater, an elastic vessel with temperature-regulated fluid circulating within the culture vessel, and the like. In the illustrated embodiment, the heating component 30 is conformally disposed around the culture vessel and provides thermal contact with the culture vessel 12. In one example, the heating component 30 may have a flexible and conformal structure. In a non-limiting example, the heating component 30 may be a thin film heater. In one embodiment, the heating component 30 is made of one or more thin sheets of electrically conductive materials, such as, metals (for example, aluminum, copper, and the like), electrically conductive ceramic composites, electrically conductive polymers, and the like and combinations thereof. Alternatively, the heating component 30 may form an integral part of the culture vessel 12, e.g. as a jacket of a double-walled culture vessel. It is then possible to circulate a temperature-control liquid through the jacket for heating and/or cooling as needed to maintain a constant predetermined temperature inside the culture vessel. Cooling is primarily needed in the case where microbial cells are cultivated in the vessel, due to the heat generated by the cell metabolism.

The air introducing unit or sparger 16 is operatively coupled to the culture vessel 12 and configured to inject air 40 into the culture vessel 12. In one embodiment, the air introducing unit or sparger 16 includes at least one air introducing nozzle 36 and at least one conduit 38 coupled to the air introducing nozzle 36. Alternatively, the air introducing unit or sparger 16 may comprise one or more porous bodies and at least one conduit coupled to the one or more porous bodies. In the illustrated embodiment, the at least one conduit 38 is inserted via a port or hole (not shown in FIG. 1) formed in the culture vessel 12. The conduit 38 is configured to receive air 40 from an air or gas source 41 and inject the air 40 in the culture vessel 12 using the air introducing nozzle 36 or the one or more porous bodies. In the illustrated embodiment, the air introducing nozzle 36 is disposed on the bottom portion 28 of the culture vessel 12. However, other locations of the air introducing nozzle 36 and conduit 38 are envisioned within the purview of the present specification.

In one or more embodiments, the air 40 injected in the culture vessel 12 results in formation of air bubbles 42 within the culture vessel 12. The at least one impeller 18 is disposed within the culture vessel 12 and configured to stir at least a portion of the cell-culture media 22 and the plurality of cells 20 to facilitate uniform dispersion of the air bubbles 42 in the culture vessel 12. In some embodiments, the impeller 18 includes a hub 44 and a plurality of blades 46 coupled to the hub 44. In the illustrated embodiment, the plurality of blades 46 is disposed along the circumferential direction 48 of the hub 44 (or the culture vessel 12) and spaced apart from each other. Each blade 46 of the plurality of blades 46 is coupled to at least a portion of a circumference 50 of the hub 44. Further, each blade 46 includes a pressure face 52 and a suction face 54. It should be noted herein that the pressure face 52 and the suction face 54 are defined relative to a direction of rotation 56 of the impeller 18.

In some embodiments, the at least one impeller 18 is operatively coupled to a drive unit 58, such as a motor or a magnetic drive, e.g. via a shaft 60. Specifically, the hub 44 may include a slot or opening or hole (not shown in FIG. 1) configured to receive the shaft 60. If the at least one impeller 18 is magnetically driven, the slot/opening/hole may not be needed, which is advantageous for maintaining sterility inside the culture vessel. In the illustrated embodiment, the drive unit 58 is disposed on the top portion 26 of the culture vessel 12 and the shaft 60 is inserted via a port or hole (not shown in FIG. 1) formed in the culture vessel 12. Although not illustrated, in alternative embodiments, the drive unit 58 may be disposed on the bottom portion 28 of the culture vessel 12 and coupled to the impeller 18 via the shaft 60. The drive unit 58 is further coupled to the power source 32 of the heating assembly 14. The drive unit 58 is configured to receive electrical power from the power source 32 for rotating the impeller 18 along the circumferential direction.

The drive unit and the heating component 30 may or may not share a common power source 32. In certain embodiments, the bioreactor system 10 may include electromagnets coupled to the shaft 60 and the power source 32. In some of these embodiments, the power source 32 is configured to supply electrical power to the electromagnets for rotating the impeller 18.

In certain embodiments, the bioreactor system 10 may include a plurality of impellers 18a, 18b, 18c spaced apart from each other along an axial direction 162 of the bioreactor system 10 and coupled to the shaft 60. In such an embodiment, each impeller of the plurality of impellers may be configured to be in contact with the cell-culture media 22 and the plurality of cells 20.

In the illustrated embodiment, the at least one impeller 18 is a radial flow impeller. The blades 46 may in this case suitably be vertically oriented. In a particular embodiment, the radial flow impeller is a modified Rushton impeller. Conventionally, the Rushton impeller is a flat blade radial flow impeller. In one or more embodiments, the hub 44 may have a planar or a non-planar surface. Further, the plurality of blades 46 may have a planar or a non-planar surface. In the illustrated embodiment, the hub 44 is a flat-disc shaped component and each blade of the plurality of blades 46 is a flat-square or flat-rectangular shaped component, which is vertically mounted to the hub 44. The illustrated shapes of the hub 44 and the blades 46 illustrated in FIG. 1 are exemplary and should not be construed as a limitation of the present specification. By way of example, although not illustrated, in certain embodiments, the hub 44 may be a flat-square or flat-rectangular shaped component and each blade 46 may be a flat-disc shaped component depending on the application and design criteria. In some embodiments, the culture vessel 12 and the impeller 18 together constitute a bioreactor sub-system 19. In one or more embodiments, the impeller 18 includes one or more turbulators 64 disposed on at least a portion of the suction face 54 of a blade of the plurality of blades 46. In certain embodiments, the one or more turbulators 64 may include a rib, a groove, a dimple, a through-opening, a protrusion, or combinations thereof. The one or more turbulators 64 are discussed in greater detail below.

It may be noted herein that the one or more turbulators 64 disposed on the blade 46 may or may not be parallel to one another. Further, the one or more turbulators 64 may be disposed parallel to a tip edge or may be at an angle in a range from about 0 degrees to about 90 degrees to the tip edge. Additionally, each of the one or more turbulators 64 may include a continuous portion or a single component. However, although not illustrated, in some other embodiments, one or more turbulators 64 may include discontinuous portions or patterned portions that together constitute one or more turbulators 64. Further, the one or more turbulators 64 may be made of single or multiple layers.

During operation of the bioreactor system 10, the heating component 30 conducts heat to the cell-culture media 22 via the culture vessel 12. The air introducing nozzle 36 injects air 40 into the cell-culture media 22, which results in formation of the air bubbles 42. The impeller 18 rotates and provides agitation to the cell-culture media 22 and the plurality of cells 20 along the circumferential direction to uniformly distribute air 40 (i.e., via the air bubbles 42) for the growth of the plurality of cells 20. In such embodiments, the one or more turbulators 64 are configured to generate turbulence at the suction face 54 and prevent the air bubbles 42 to coalesce and/or stick to the suction face 54. Thus, the bioreactor system 10 is configured to increase an interfacial area (i.e., area density) between the air 40 and the cell-culture media 22, thereby increasing an oxygen (i.e., present in the air 40) transfer rate for growth of the plurality of cells 20 in the cell-culture media 22.

Figure 2:
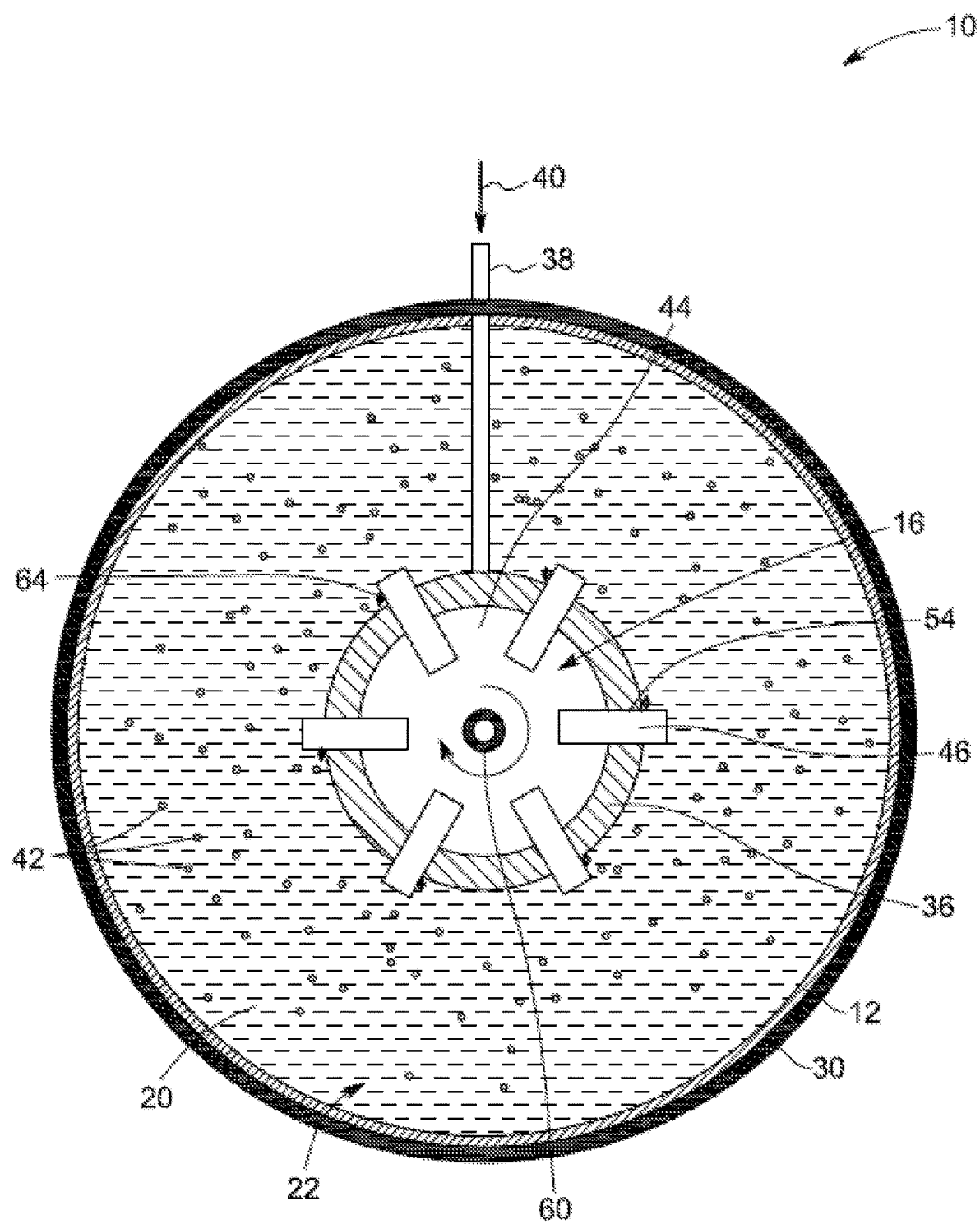
FIG. 2 is a schematic top view of the bioreactor system of FIG. 1, in accordance with aspects of the present technique.

FIG. 2 is a schematic top view of the bioreactor system 10 of FIG. 1 in accordance with some embodiments of the present specification. In the illustrated embodiment, the plurality of cells 20 and the cell-culture media 22 are filled in the culture vessel 12. The heating component 30 encompasses the culture vessel 12. The air introducing nozzle 36 is disposed within the culture vessel 12. In the illustrated embodiment, the air introducing nozzle 36 has a circular cross-section, however, other shapes of the cross-section of the air introducing nozzle 36 are also envisioned within the purview of this specification. By way of example, the shape of the cross-section of the air introducing nozzle 36 may be based on a cross-section of the culture vessel 12. Further, the impeller 18 may be operatively coupled to the culture vessel 12 via the shaft 60 such that the plurality of blades 46 and the hub 44 are in contact with at least a portion of the plurality of cells 20 and the cell-culture media 22. During operation, the air bubbles 42 tend to accumulate at the suction face 54 and the one or more turbulators 64 are configured to generate turbulence at the suction face 54, the turbulence generated by the turbulators in the form of eddies prevent the air bubbles 42 to coalesce and/or stick to the suction face 54. In some embodiments, the impeller 18 and the heating component 30 facilitates maintaining the one or more internal parameters, such as the pH level, DO level, and temperature of the cell-culture media 22. Maintaining the internal parameters to desirable values results in improved efficiency of the bioreactor system 10.

Figure 3:
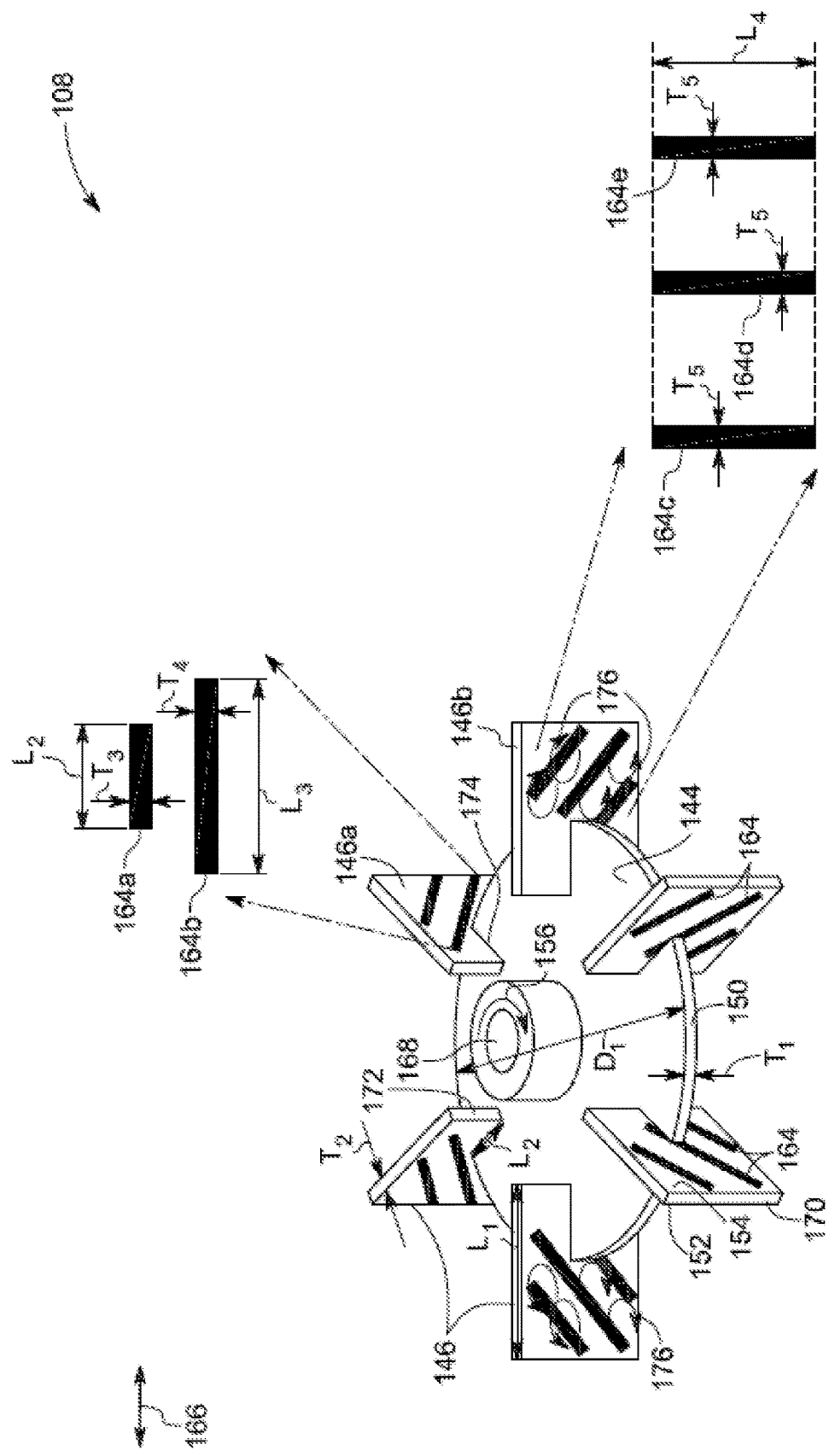
FIG. 3 is a perspective view of an impeller having one or more turbulators, such as ribs, disposed on a suction face of a plurality of blades, in accordance with aspects of the present technique.

FIG. 3 is a perspective view of an example impeller 108 in accordance with one exemplary embodiment of the present technique. In the illustrated embodiment, the impeller 108 includes a hub 144 and a plurality of blades 146.

In some embodiments, the hub 144 is a flat-disc shaped component having a thickness "$T_1$" smaller than a diameter "D". The hub 144 may include a slot 168 or other shaft fitting disposed at a center for receiving a shaft coupled to the motor or a magnetic drive. Each blade of the plurality of blades 146 is a flat-square or a flat-rectangular shaped component having a thickness "$T_2$" smaller than a length "$L_1$". Each blade 146 includes a pressure face 152 and a suction face 154, which are defined relative to a direction of rotation 156 of the impeller 108. Further, each blade 146 includes a tip edge 170 and a hub edge 172. Each blade 146 includes a slot 174 extending from the hub edge 172 to the tip edge 170 up to a determined length "$L_2$". In the illustrated embodiment, the slot 174 extends from a center of the hub edge 172. The blades 146 are spaced apart from each other and coupled to at least a portion of a circumference 150 of the hub 144. In one embodiment, the slot 174 is snap-fitted to the circumference 150 of the hub 144. In the illustrated embodiment, the impeller 108 includes one or more ribs 164 disposed on at least a portion of the suction face 154 of each blade of the plurality of blades 146. The one or more ribs 164 are coupled to the suction face 154 via brazing, welding, and the like. In such an embodiment, the one or more ribs 164 are made of a first material and the plurality of blades 146 is made of a second material different from the first material. In some embodiments, the one or more ribs 164 and each blade 146 are integral components of a blade 146. In such an embodiment, the one or more ribs 164 and the plurality of blades 146 are made of same material. In the illustrated embodiment, each blade 146 includes three ribs 164, which are disposed proximate to the tip edge 170 and coupled to the suction face 154. The one or more ribs 164 are arranged in a form of an array of ribs on the suction face 154. Non-limiting example of arrays of turbulators may include 1×2, 2×2, 2×3, 2×4, and the like, based on desirable amount of eddies and size of the turbulators. In the illustrated embodiment, each rib of the one or more ribs 164 has smooth edges. Advantageously, smooth edges facilitate prevention of coalescing of air bubbles while avoiding undesirable shearing of the plurality of cells during rotation of the impeller 108. Various ribs 164 disposed on a particular blade 146 may have same or different dimensions. In one example, at least one rib of the one or more ribs 164 of a particular blade 146 may have a thickness, a length, or both that are different from thicknesses, lengths, or both of other ribs of the one or more ribs 164. For example, a blade 146a includes a rib 164a having a length "$L_2$" and thickness "$T_3$" and rib 164b having a length "$L_3$" and thickness "$T_4$" different from the length "$L_2$" and thickness "$T_3$". However, a blade 146b includes a plurality of ribs 164c, 164d, 164e, where each rib of plurality of ribs 164c, 164d, 164e has a substantially same length "$L_4$" and thickness "$T_5$". In one embodiment, the ribs 164 on a particular blade 146 may occupy about 20 percent to about 40 percent of an area of a single surface, such as the suction face, of that particular blade 146.

Figure 4:
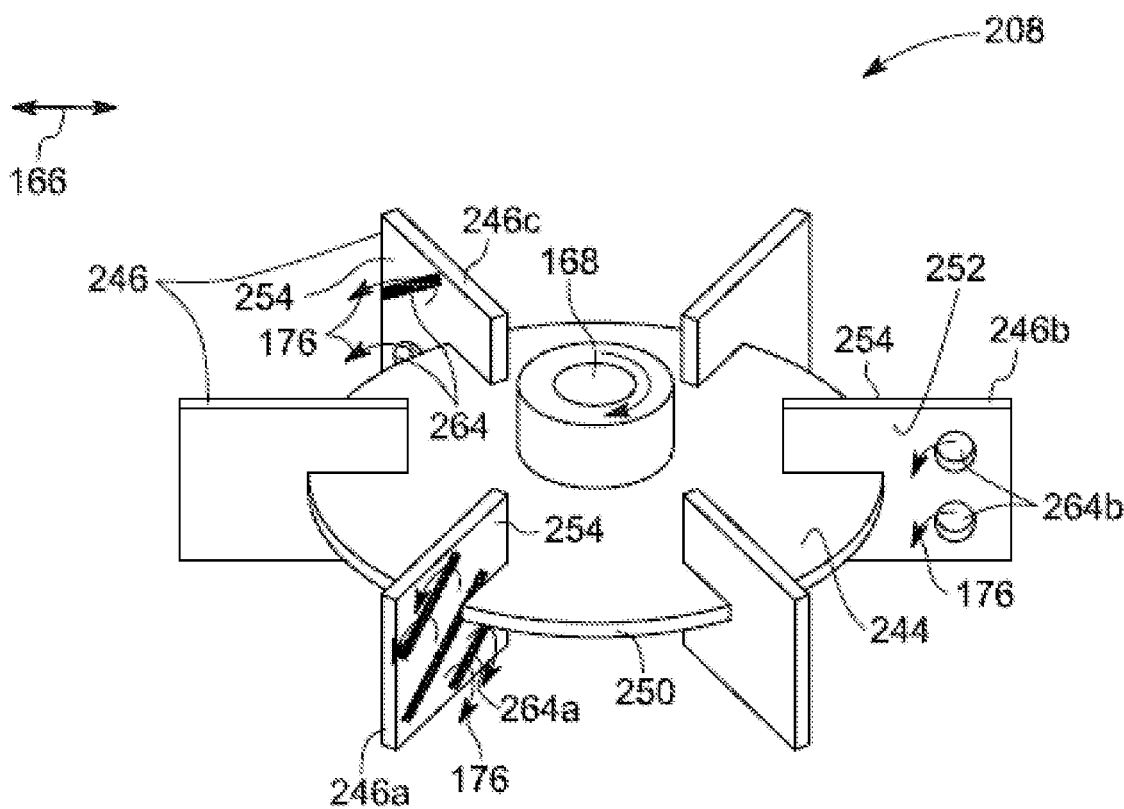
FIG. 4 is a perspective view of an impeller having one or more turbulators disposed on alternate blades of a plurality of blades, in accordance with aspects of the present technique.

It may be noted that the ribs 164 disposed on any particular blade 146 may or may not be parallel to one another. Further, the ribs 164 may be disposed parallel to the tip edge 170 or may be at an angle in a range from about 30 degrees to about 150 degrees to the tip edge 170. Additionally, each rib 164 may include a continuous portion as illustrated in FIG. 4, however, although not illustrated, in some other embodiments, one or more ribs 164 may include discontinuous or patterned portions that together constitute a rib 164. Further, the ribs 164 may be made of single or multiple layers.

During operation, as the impeller 108 rotates, the air bubbles tend to entrain and stick to the suction face 154 due to a low-pressure at the suction face 154. Further, the air bubbles tend to coalesce to each other on the suction face 154. The ribs 164 are used to minimize or prevent coalescing of the air bubbles at the suction face 154. In particular, the ribs 164 cause a portion of the cell-culture media to flow along a radial direction 166 of the bioreactor system 100. The flow of the cell-culture media along the radial direction 166 causes generation of eddies, generally represented by reference numeral 176, around the suction face 154, thereby preventing the air bubbles from coalescing and/or sticking to the suction face 154 of the blade 146. Advantageously, the eddies 176 result in breaking the air bubbles without damaging, such as shearing, the plurality of cells.

FIG. 4 is a perspective view of an example impeller 208 in accordance with one exemplary embodiment of the present technique. In the illustrated embodiment, the impeller 208 includes a hub 244 and a plurality of blades 246 spaced apart from each other and coupled to at least a portion of a circumference 250 of the hub 244.

In one embodiment, the impeller 208 includes one or more turbulators 264 disposed on alternate blades 246a, 246b, and 246c of the plurality of blades 246. Further, the alternate blades 246a, 246b, and 246c having the turbulators may have same or different turbulators. In the illustrated embodiment, the impeller 208 includes one or more ribs 264a coupled to a suction face 254 of the blade 246a of the plurality of blades 246. The impeller 208 includes one or more through-openings 264b extending between a suction face 254 and a pressure face 252 of the blade 246b of the plurality of blades 246. Further, the impeller 208 includes one rib 264a coupled to a suction face 254 of the blade 246c of the plurality of blades 246 and one through-opening 264b extending between the suction face 254 and a pressure face 252 of the blade 246c. In the illustrated embodiment, the one or more ribs 264a are arranged in a form of an array of ribs on the suction face 254 of the blade 246a and the one or more through-openings 264b are arranged in a form of an array of through-openings on the suction face 254 of the blade 246b.

During operation, the one or more ribs 264a cause a portion of the cell-culture media to flow along a radial direction 166 of the bioreactor system. The flow of the cell-culture media along the radial direction 166 causes generation of eddies 176 around the suction face 254 of the blades 246a, 246c. Similarly, the one or more through-openings 264b cause the portion of the cell-culture media to flow from the pressure face 252 to the suction face 254 via the one or more through-openings 264b. The flow of the cell-culture media through the one or more through-openings 264b cause generation of eddies 176 around the suction face 254 of the blades 246b, 246c. Thus, the eddies 176 prevent air bubbles to coalesce and/or stick to the suction face 254. Advantageously, the eddies 176 result in breaking the air bubbles without damaging, such as shearing, the plurality of cells.

FIGS. 3 and 4 illustrate alternative embodiments of an impeller of the present specification. However, it may be noted that several other configurations with respect to blades and turbulators are also envisioned within the purview of this specification. By way of example, in the impeller 108 of FIG. 3, different blades 146 may have ribs 164a of different numbers, sizes, patterns, orientations, and combinations thereof. Similarly, in the impeller 208 of FIG. 4, blades 246a, 246b, and 246c may have different turbulators than illustrated, for example, the blade 246c may have dimples, protrusions, and the like.

Figure 5:
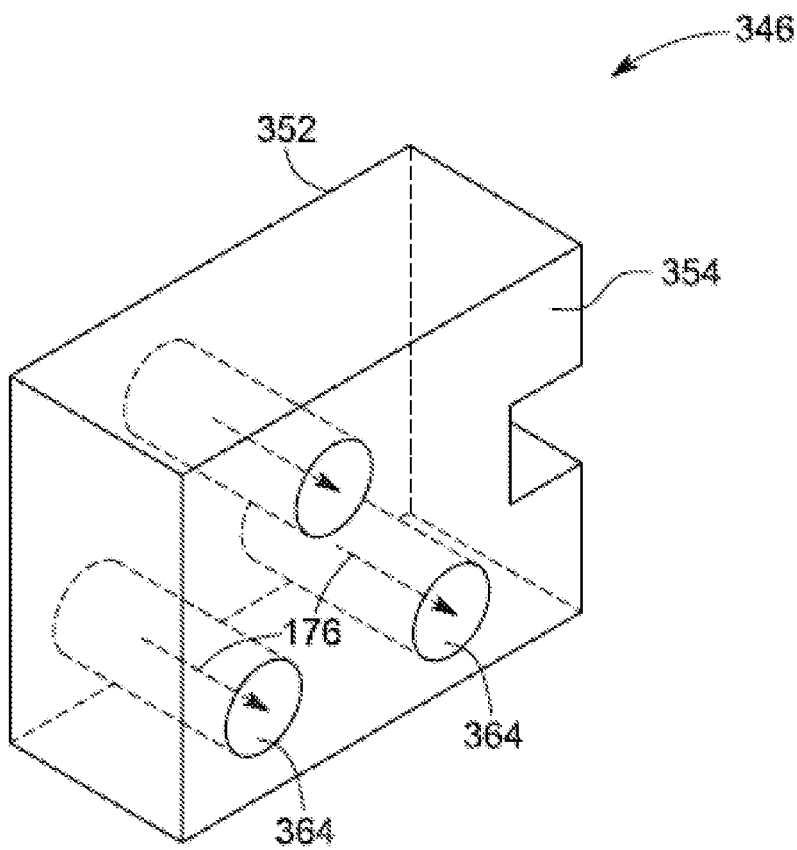
FIG. 5 is a perspective view of a blade having one or more through-openings, in accordance with aspects of the present technique.

FIG. 5 is a perspective view of an example blade 346 and one or more through-openings 364 in accordance with one exemplary embodiment of the present technique. The one or more through-openings 364 extend between a suction face 354 and the pressure face 342 of the blade 346. In the illustrated embodiment, the through-openings 364 are arranged in a form of an array of through-openings on the suction face 354. In the illustrated embodiment, each through-opening of the one or more through-openings 364 has an equal diameter. In some other embodiments, each of the one or more through-openings 364 may have different values for diameters. Further, the one or more through-openings 364 are shown to have a circular shaped profile, however, one or more through-openings 364 may have other cross-sections, such as, rectangular, square, oval, and the like. During operation, a portion of the cell-culture media flows from the pressure face 352 to the suction face 354 via the one or more through-openings 364. The flow of the cell-culture media through the one or more through-openings 364 cause generation of eddies 176 around the suction face 354, thereby preventing air bubbles to coalesce and/or stick to the suction face 354. Advantageously, the eddies 176 result in breaking the air bubbles without damaging, such as shearing, the plurality of cells.

Figure 6:
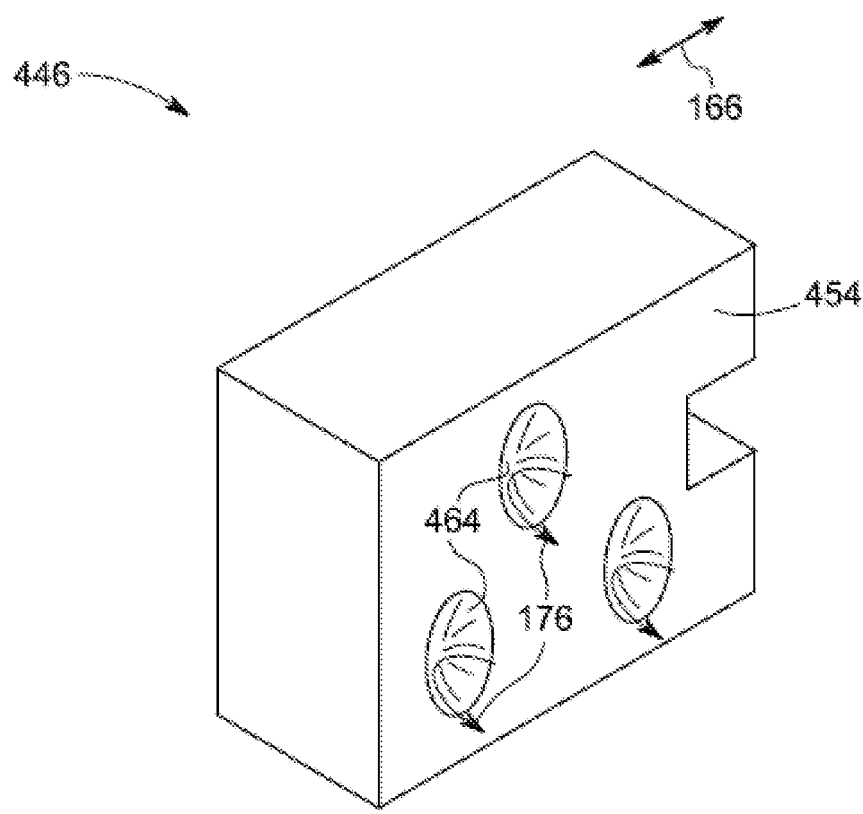
FIG. 6 is a perspective view of a blade having one or more dimples, in accordance with aspects of the present technique.

FIG. 6 is a perspective view of an example blade 446 and one or more dimples 464 in accordance with one exemplary embodiment of the present technique. The one or more dimples 464 are disposed on a suction face 454 of the blade 446. In the illustrated embodiment, the one or more dimples 464 are arranged in a form of an array of dimples on the suction face 454. In one embodiment, each of the one or more dimples 464 may or may not have similar dimensions and cross-sections. For example, in certain embodiments, each of the one or more dimples 464 may have different depths. During operation, the one or more dimples 464 causes a portion of the cell-culture media to flow along a radial direction 166 causes generation of eddies 176 around the suction face 454 of the blade 446, thereby preventing air bubbles to coalesce and/or stick to the suction face 454. Advantageously, the eddies 176 result in breaking the air bubbles without damaging, such as shearing, the plurality of cells.

Figure 7:
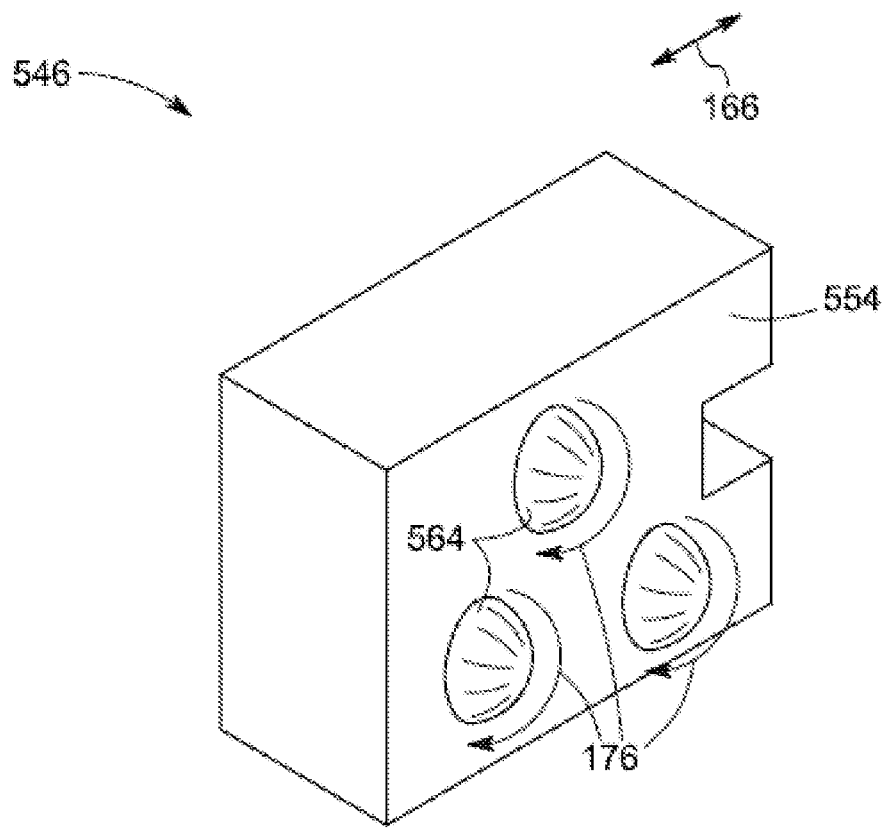
FIG. 7 is a perspective view of a blade having one or more protrusions, in accordance with aspects of the present technique.

FIG. 7 is a perspective view of an example blade 546 and one or more protrusions 564 in accordance with one exemplary embodiment of the present specification. The one or more protrusions 564 are disposed on a suction face 554 of the blade 546. In the illustrated embodiment, the one or more protrusions 564 are arranged in a form of an array of protrusions on the suction face 554. In certain embodiments, the protrusions 564 may have same thickness. In certain other embodiments, one or more of the protrusions 564 may have thicknesses that are different from thicknesses of other protrusions 564. During operation, the one or more protrusions 564 causes a portion of the cell-culture media to flow along a radial direction 166, thereby generating of eddies 176 around the suction face 554 of the blade 546, thereby preventing air bubbles to coalesce and/or stick to the suction face 554. Advantageously, the eddies 176 result in breaking the air bubbles without damaging, such as shearing, the plurality of cells.

Figure 8:
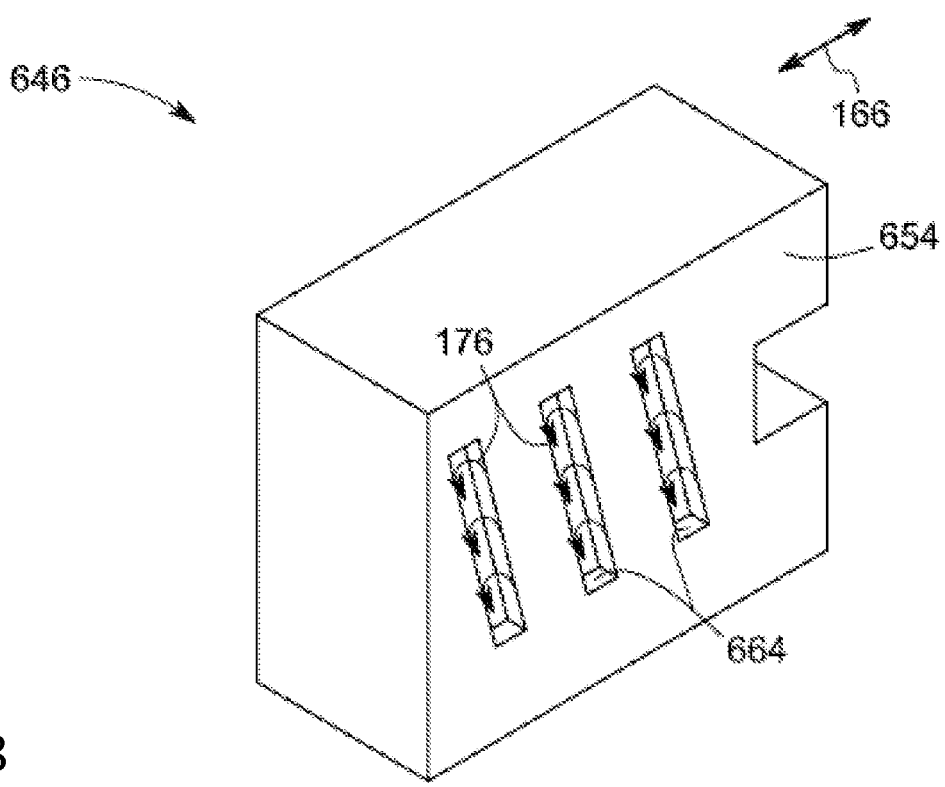
FIG. 8 is a perspective view of a blade and one or more grooves, in accordance with aspects of the present technique.

FIG. 8 is a perspective view of an example blade 646 and one or more grooves 664 in accordance with one exemplary embodiment of the present specification. The one or more grooves 664 are disposed on a suction face 654 of the blade 646. In the illustrated embodiment, the one or more grooves 664 are arranged in a form of an array of grooves on the suction face 654. In certain embodiments, each of the grooves 664 have same dimensions. In certain other embodiments, one or more grooves 664 may have dimensions that are different from dimensions of other grooves 664. During operation, the 664 causes a portion of the cell-culture media to flow along a radial direction 166, thereby generating eddies 176 around the suction face 654 of the blade 646. Presence of eddies proximate the suction face 654 prevents air bubbles to coalesce and/or stick to the suction face 654. Advantageously, the eddies 176 result in breaking the air bubbles without damaging, such as shearing, the plurality of cells.

Figure 9:
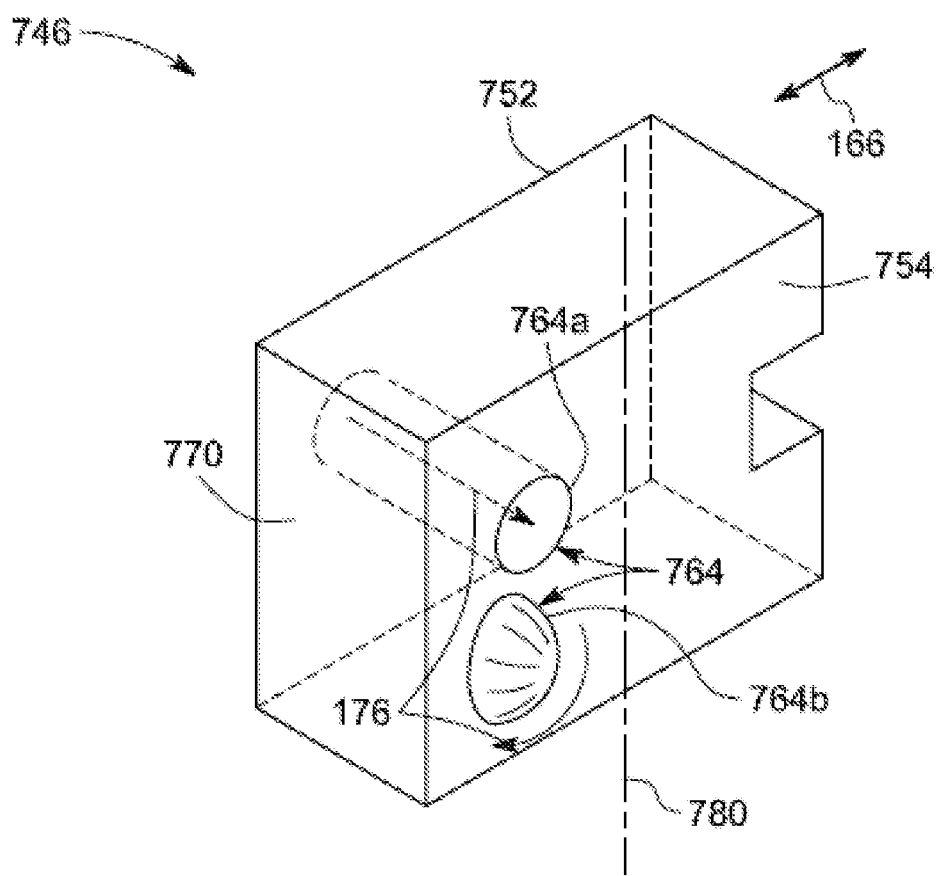
FIG. 9 is a perspective view of a blade having two different turbulators, in accordance with aspects of the present technique.

FIG. 9 is a perspective view of an example blade 746 and a plurality of turbulators 764 in accordance with one exemplary embodiment of the present specification. In the illustrated embodiment, the plurality of turbulators 764 includes a through-opening 764a and a protrusion 764b. The through-opening 764a extends between a suction face 754 and a pressure face 752, and the protrusion 764b is disposed on a suction face 754 of the blade 746. In the illustrated embodiment, the plurality of turbulators 764 is disposed only in 50 percent of a surface area of the blade 746 from a center line 780 of the blade 746 towards the tip edge 770. During operation, the one or more turbulators 764 generate turbulence around the suction face 754, the turbulence enhances mixing of air with a plurality of cells in a cell-culture media.

Figure 10A:
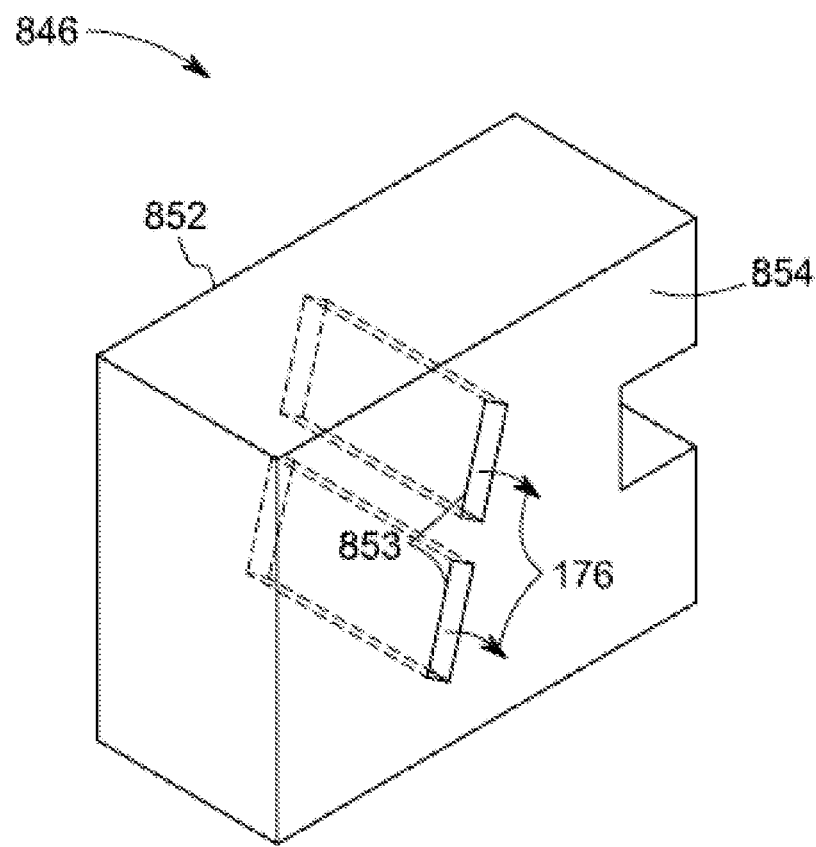
FIG. 10A is a perspective view of a blade having a plurality of first openings, in accordance with aspects of the present technique.
Figure 10B:
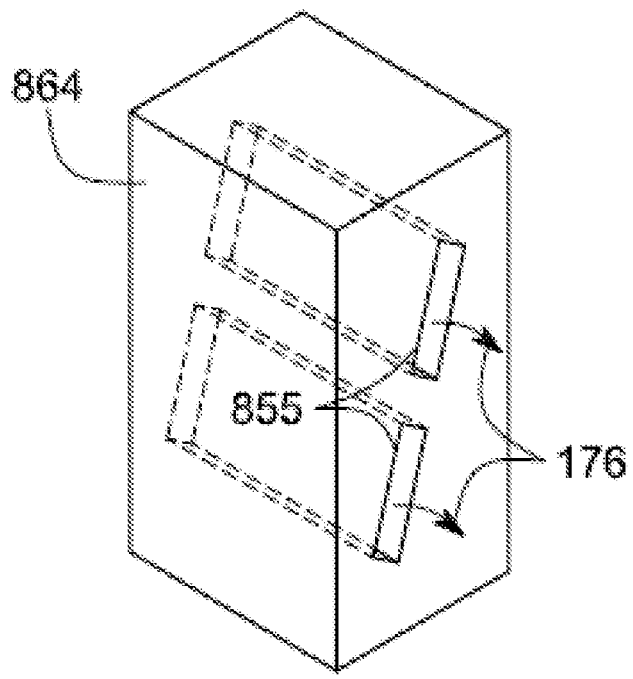
FIG. 10B is a perspective view of a turbulator having a plurality of second openings, in accordance with aspects of the present technique.

FIGS. 10A and 10B is a perspective view of an example blade 846 having a rib 864 in accordance with one exemplary embodiment of the present specification. In one embodiment, the impeller includes the blade 846 having a plurality of first through-openings 853, where each first through-opening 853 extends between a suction face 854 and a pressure face 852 of the blade 846. The rib 864 includes a plurality of second through-openings 855. In the illustrated embodiment, the first and second through-openings 853, 855 have a rectangular shape. The rib 864a is configured to be coupled to the suction face 854 such that each second through-opening 855 is aligned with a corresponding first through-opening 853. During operation, each of the first and second through-openings 853, 855 causes a portion of the cell-culture media to flow from the pressure face 852 to the suction face 854. The flow of the cell-culture media through the first and second through-openings 853, 855 causes generation of eddies 176 around the suction face 854, thereby preventing air bubbles to coalesce and/or stick to the suction face 854. Advantageously, the eddies 176 result in breaking the air bubbles without damaging, such as shearing, the plurality of cells. The one or more turbulators as discussed in the embodiments of FIGS. 3 to 10 are configured to define a non-planar surface to the suction face, of the blade to generate turbulence around the suction face and prevent coalescing and/or sticking of air bubbles to the suction face.

Figure 11:
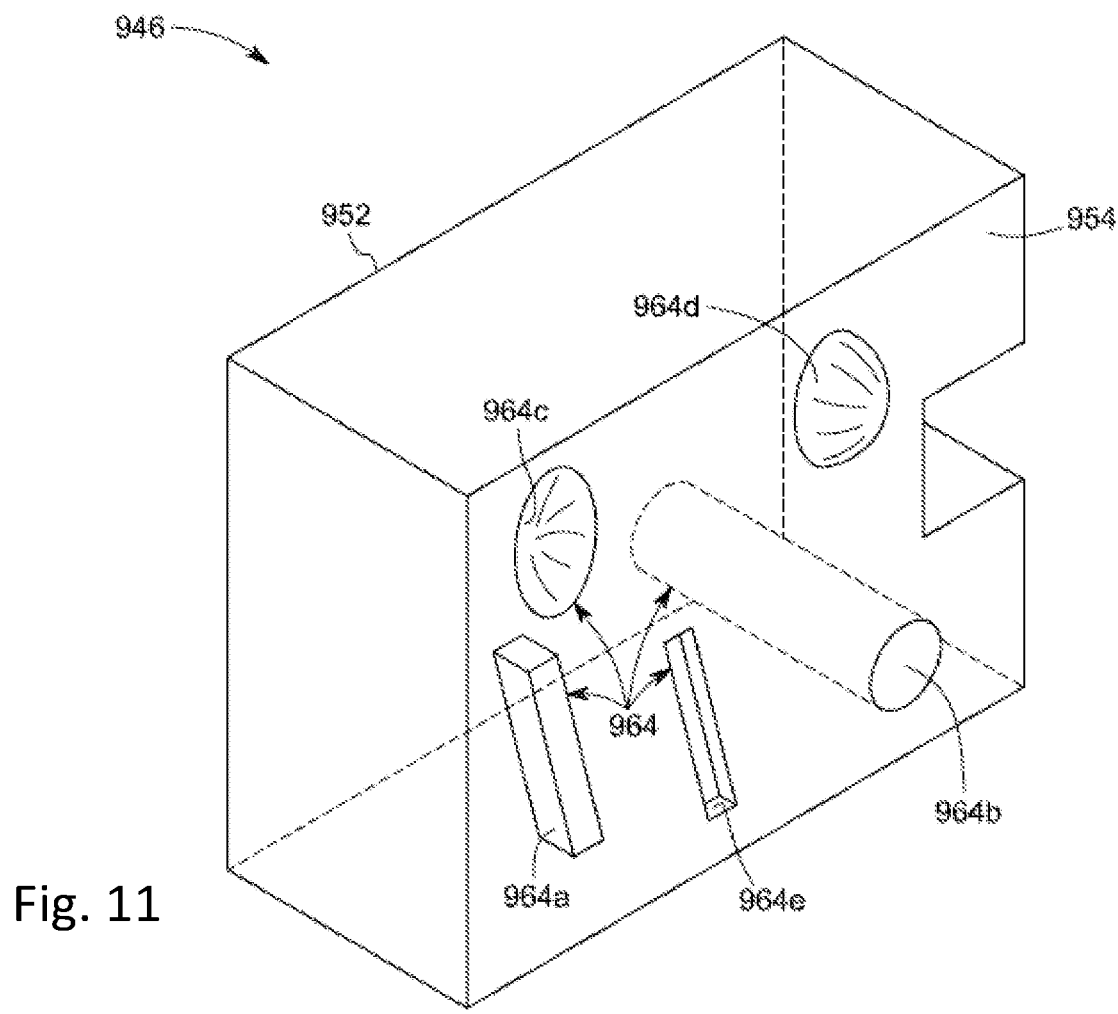
FIG. 11 is a perspective view of a blade having a plurality of turbulators disposed on the blade, in accordance with aspects of the present technique.

FIG. 11 is a perspective view of an example blade 946 and a plurality of turbulators 964 disposed on the blade 946 in accordance with one exemplary embodiment of the present specification. In one embodiment, the plurality of turbulators 964 includes a combination of different types of turbulators. The different types of turbulators may be selected based on factors, such as, but not limited to, volume of cells, volume of culture media, number of eddies desirable, rotation speed of the impeller, and the like. In the illustrated embodiment, the plurality of turbulators 964 includes a rib 964a, a through-opening 964b, a dimple 964c, a protrusion 964d, and a groove 964e. In one embodiment, the rib 964a is coupled to a suction face 954 of the blade 946. The through-opening 964b extends between the suction face 954 and a pressure face 952 of the blade 946. The dimple 964c, the protrusion 964d, and the groove 964e are disposed on the suction face 954 of the blade 946. During operation, the plurality of turbulators 964 is configured to generate turbulence at the suction face 954 and to prevent air bubbles from coalescing and/or sticking to the suction face 954.

Figure 12:
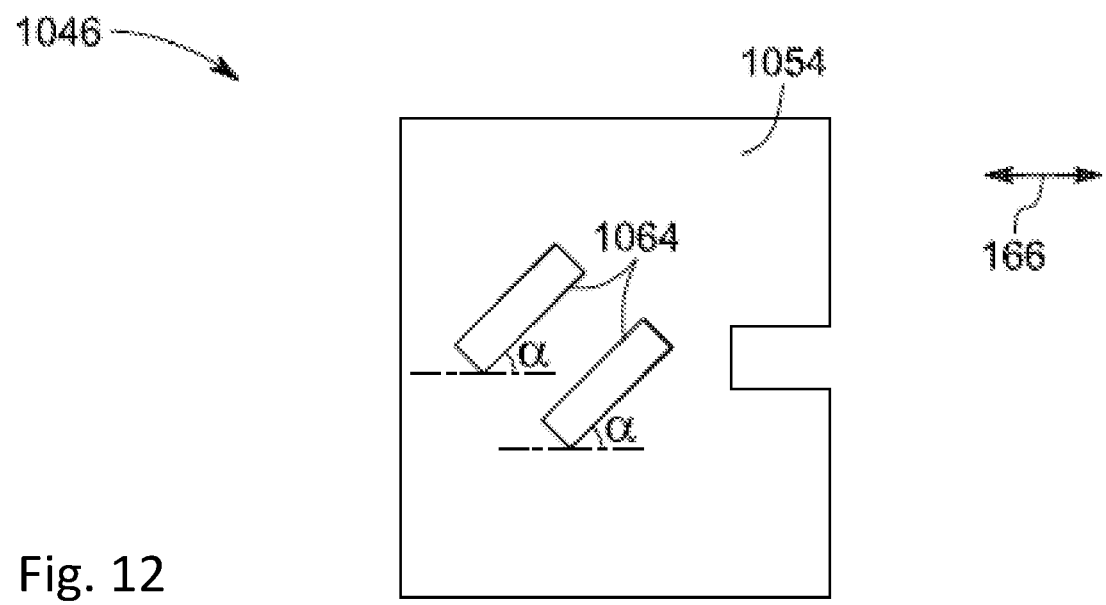
FIG. 12 is a schematic view of a blade and a plurality of ribs disposed on the blade, where ribs of the plurality of ribs are inclined at a first determined angle, in accordance with aspects of the present technique.

FIG. 12 is a schematic view of a blade 1046 and a plurality of ribs in accordance with some embodiments of the present specification. In the illustrated embodiment, the plurality of ribs 1064 is coupled to a suction face 1054 of the blade 1046. Each rib of the plurality of ribs 1064 is inclined at a determined angle "α" relative to a radial axis 166 of a hub of an impeller. In some embodiments, the determined angle "α" is in a range from about 30 degrees to about 150 degrees. In the illustrated embodiment, the determined angle "α" is at 30 degrees. Further, each rib of the plurality of ribs 1064 has a flat and smooth surface. In one embodiment, each rib 1064 which is inclined at the determined angle "α" generates a turbulence at the suction face 1054 and prevents air bubbles from coalescing and/or sticking to the suction face 1054. Further, each rib 1064 uniformly disperses the air bubbles within a culture vessel to provide substantial quantity of oxygen to the growth of a plurality of cells. In certain embodiments, the impeller may include a plurality of grooves may be disposed on the suction face 1054 of the blade 1046. In such embodiments, each groove may be inclined at the determined angle "α" relative to a radial axis 166 of the hub. In some embodiments, the determined angle "α" may be in a range from about 30 degrees to about 150 degrees.

Figure 13:
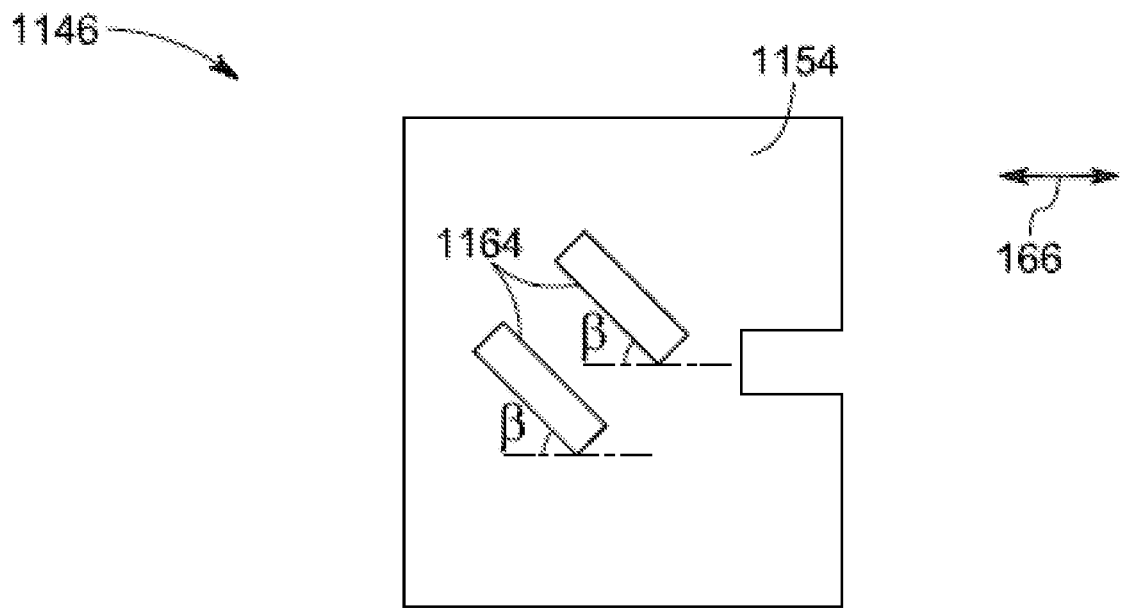
FIG. 13 is a schematic view of a blade having a plurality of ribs disposed on the blade, where ribs of the plurality of ribs are inclined at a second determined angle, in accordance with aspects of the present technique.

FIG. 13 is a schematic view of a blade 1146 and a plurality of ribs 1164 in accordance with one exemplary embodiment of the present specification. In the illustrated embodiment, the plurality of ribs 1164 is coupled to a suction face 1154 of the blade 1146. Each rib of the plurality of ribs 1164 is inclined at a determined angle "β" relative to a radial axis 166 of a hub of an impeller. In some embodiments, the determined angle "β" is in a range from about 30 degrees to about 150 degrees. In the illustrated embodiment, the determined angle "β" is at 150 degrees. In one embodiment, each rib 1164 which is inclined at the determined angle "β" generates turbulence at the suction face 1154 and prevents air bubbles to coalesce and/or stick to the suction face 1154. Further, each rib 1164 uniformly disperse the air bubbles within a culture vessel to provide substantial quantity of oxygen to the growth of a plurality of cells. In some embodiments, the determined angles "α", "β" may be selected based on number of eddies desirable, rotation speed of the impeller, uniform distribution of the air to the cell-culture media, or combinations thereof.

Figure 14:
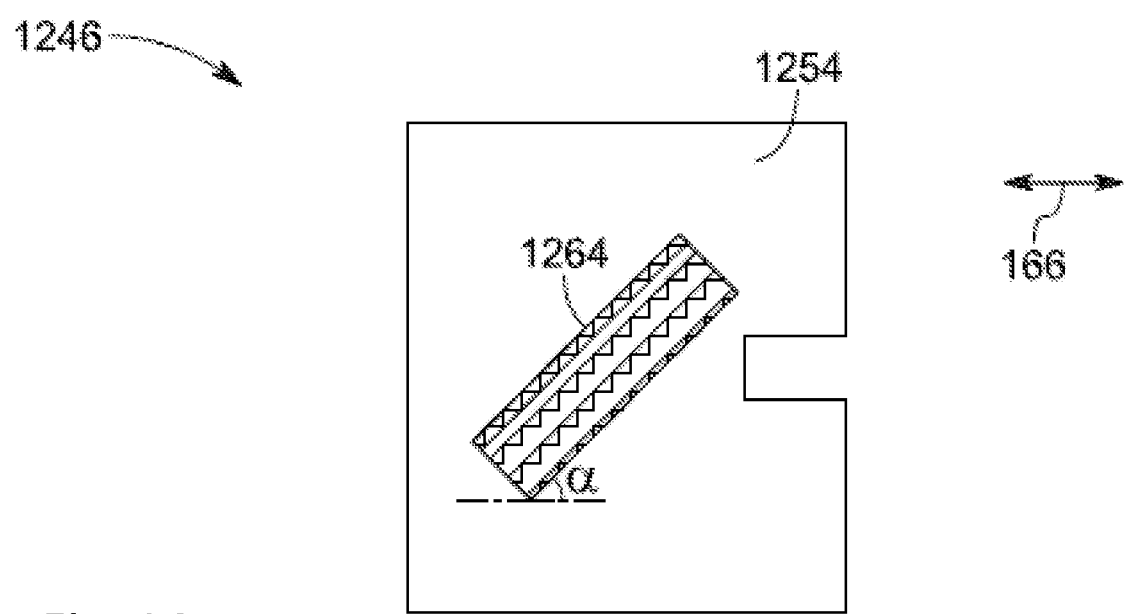
FIG. 14 is a schematic view of a blade having a rib, where the rib includes a corrugated surface, in accordance with aspects of the present technique.

FIG. 14 is a schematic view of a blade 1246 and a rib 1264 in accordance with certain embodiments of the present specification. In the illustrated embodiment, the rib 1264 is coupled to a suction face 1254 of the blade 1246. The rib 1264 is inclined at a determined angle "α" relative to a radial axis 166 of a hub of the impeller. Further, the rib 1264 has a corrugated surface. Specifically, in the illustrated embodiment, an outer surface (not labeled) of the rib 1264 includes a series of parallel ridges and grooves to additionally provide a non-planar surface to the rib 1264. In one embodiment, the rib 1264 is configured to generate turbulence at the suction face 1254 and prevent air bubbles to coalesce and/or stick to the suction face 1254.

FIGS. 5-14 illustrate some embodiments of blades employing one or more turbulators, however, it may be understood that different positioning and combinations of turbulators are envisioned within the purview of this application. By way of example, in FIG. 5, the blade 346 may employ a 4×4 array of the through-openings 364. In another example, instead of employing a corrugated rib 1264, a surface of the suction face 1254 may itself be a corrugated surface.

Figure 15:
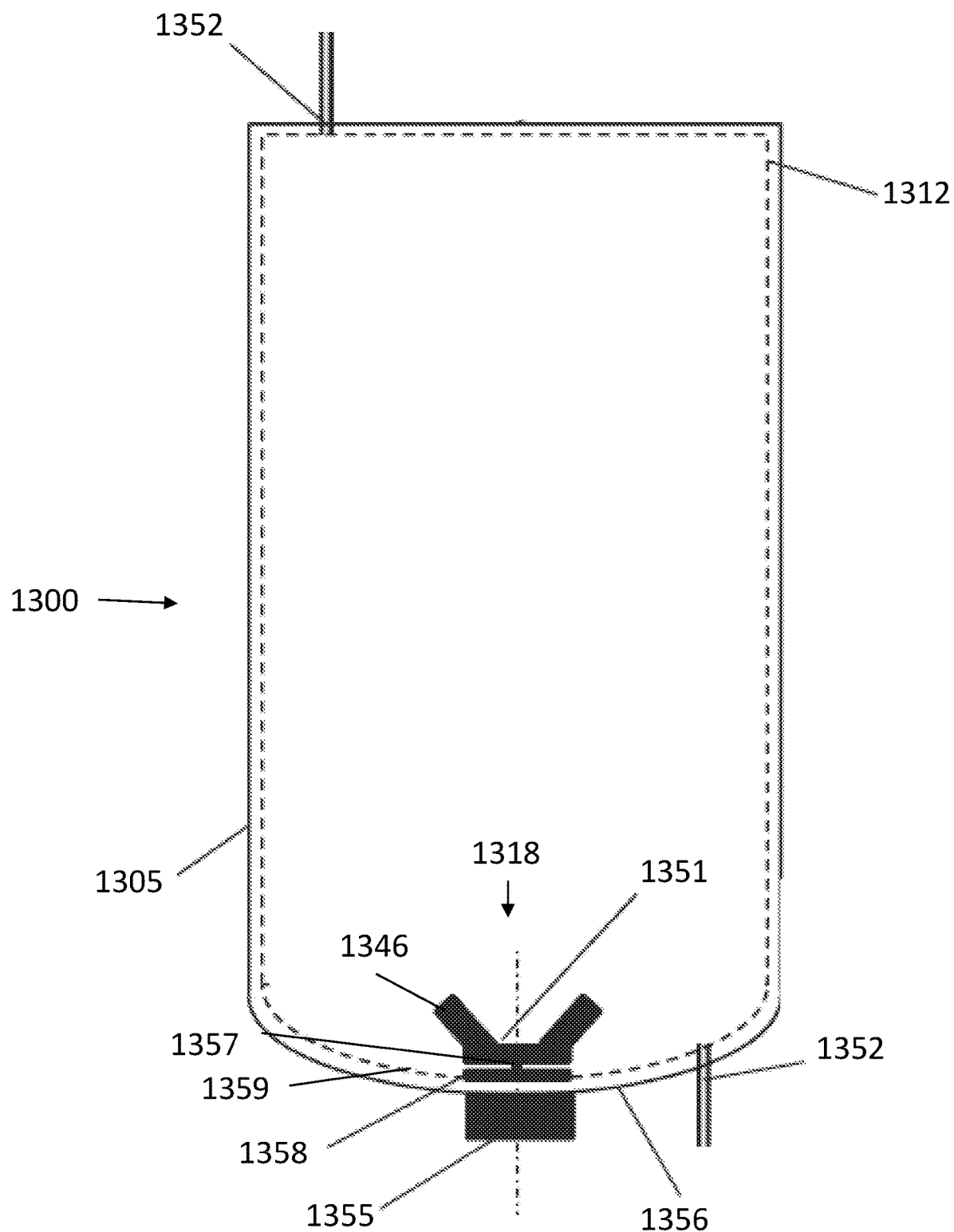
FIG. 15 is a schematic side view of a bioreactor system with a flexible bag culture vessel and a bottom-mounted magnetic impeller, in accordance with aspects of the present technique.

FIG. 15 is a schematic view of a bioreactor 1300 with a rigid support vessel 1305 and a flexible bag single use culture vessel 1312 mounted in the support vessel. The culture vessel 1312 has a bottom-mounted magnetically driven impeller 1318 with a hub 1344 and a plurality of blades 1346 coupled to a top surface 1351 of the hub. The blades comprise turbulators (not shown) as discussed above. The orientation of the blades may be vertical, but they may also be inclined with respect to a vertical plane, e.g. with an angle of 1-50 degrees, such as 10-45 degrees, to the vertical plane. The impeller is driven by a magnetic drive 1355 mounted on a bottom wall 1356 of the support vessel and aligned with the impeller, such that the impeller rotates around a shaft 1357 attached to a rigid plate 1358 welded to a bottom wall 1359 of the culture vessel. The culture vessel is equipped with a plurality of ports 1352 for entry and exit of liquids and gases before/during/after cultivation. The support vessel 1305 may further have a heating or temperature-control component (not shown), e.g. in the form of a double wall (jacket) for circulation of a temperature control liquid in order to maintain a constant predetermined temperature in the culture vessel 1312.

Figure 16:
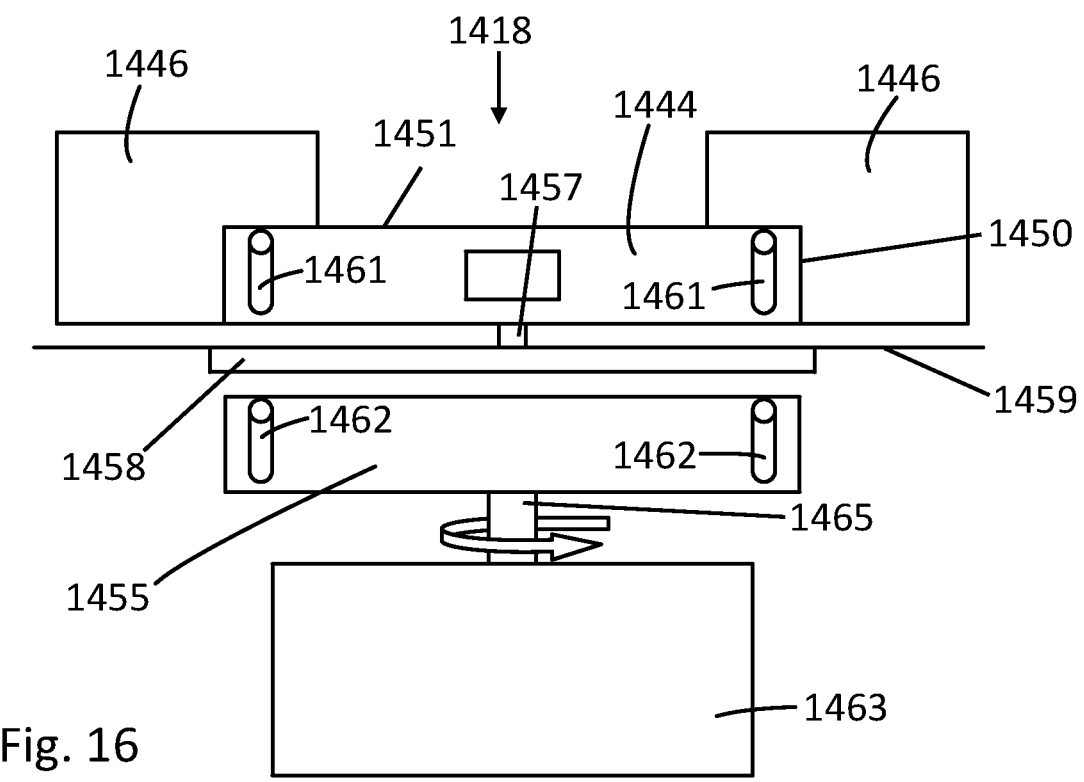
FIG. 16 is a schematic side view of a magnetically driven impeller, in accordance with aspects of the present technique.

FIG. 16 is a schematic view of a magnetically driven impeller 1418 for use e.g. in the bioreactor of FIG. 15. The impeller comprises a hub 1444 with a plurality of blades 1446 coupled to the circumference 1450 and a top surface 1451 of the hub. The blades comprise turbulators (not shown) as discussed above, while the hub comprises a plurality of impeller magnets 1461. The orientation of the blades may be vertical, but they may also be inclined with respect to a vertical plane, e.g. with an angle of 1-50 degrees, such as 10-45 degrees, to the vertical plane. The impeller is driven by a rotating magnetic drive 1455 mounted on a bottom wall of the support vessel and aligned with the impeller, such that the impeller rotates around a shaft 1457 attached to a rigid plate 1458 welded to a bottom wall 1459 of the flexible culture vessel. Alternatively, the impeller can be attached to, or integrally formed with, a shaft rotatably attached to plate 1458. The magnetic drive comprises a plurality of drive magnets 1462 and is rotated by means of a drive motor 1463 and a drive shaft 1465.

Figure 17:
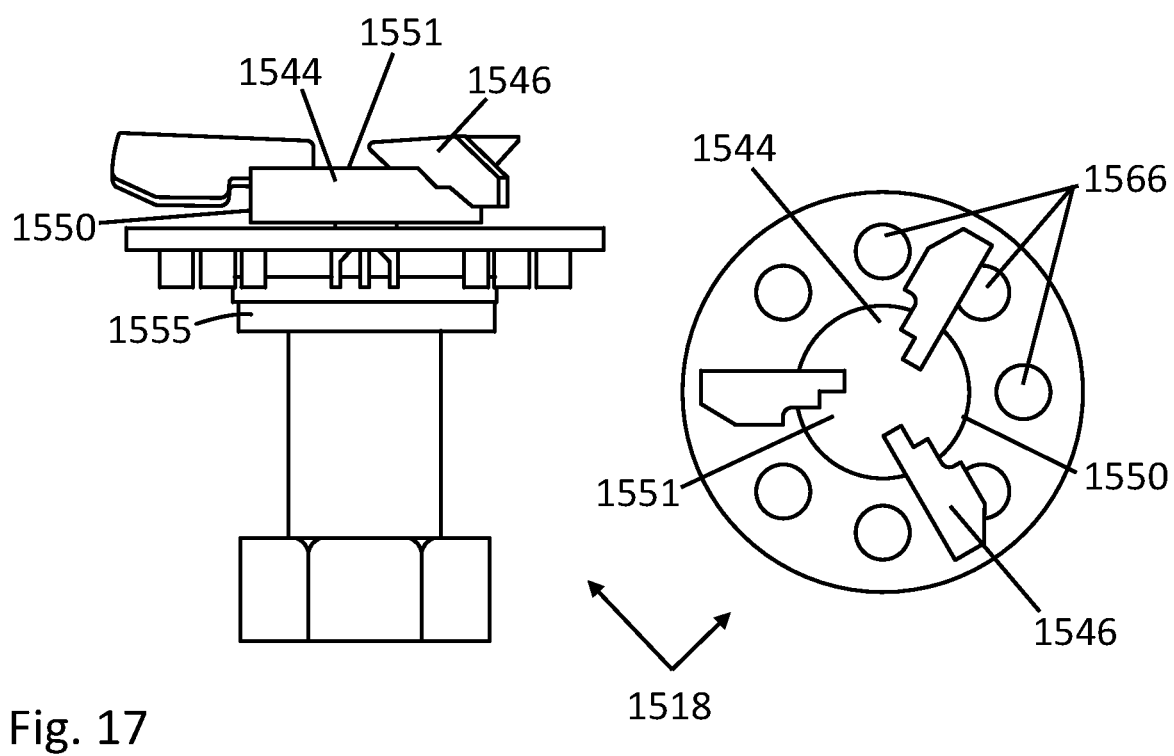
FIG. 17 shows schematic side and top views of a magnetically driven impeller with porous sparger plates, in accordance with aspects of the present technique.

FIG. 17 schematically shows a further magnetically driven impeller 1518 for use e.g. in the bioreactor of FIG. 15. The impeller comprises a hub 1544 with a plurality of blades 1546 coupled to the circumference 1550 and a top surface 1551 of the hub. The blades comprise turbulators (not shown) as discussed above. The impeller is driven by a rotating magnetic drive 1555 mounted on a bottom wall of the support vessel and aligned with the impeller. Air or gas is introduced to the flexible culture vessel via a plurality of porous sparger plates 1566 located below the impeller blades and connected to a gas supply via a conduit (not shown).

Advantageously, in accordance with one or more embodiments discussed herein, an impeller includes one or more turbulators to generate turbulence proximate a suction face of one or more blades. Thus, the impeller of the present specification improves performance of a bioreactor system. The one or more turbulators prevent coalescing and/or sticking of air bubbles to the suction face and further facilitate breaking of the air bubbles. Preventing coalescing or sticking of the air bubbles, increases an interfacial area (i.e., area density) between the air and the cell-culture media, which in turn increases DO levels in the cell-culture media. Higher DO levels facilitate enhanced oxygen transfer rate for the cell growth of the plurality of cells present in the cell-culture media.

While only certain features of embodiments have been illustrated and described herein, many modifications and changes will occur to those skilled in the art. It is, therefore, to be understood that the appended claims are intended to cover all such modifications and changes as falling within the spirit of the invention.

The invention claimed is:

1. An impeller for a bioreactor system, comprising:
a hub;
a plurality of blades disposed along a circumferential direction of the hub and spaced apart from each other, wherein each of the plurality of blades is coupled to at least a portion of a circumference and/or a top surface of the hub, wherein each blade of the plurality of blades comprises a pressure face and a suction face; and
one or more turbulators disposed on at least a portion of the suction face, the pressure face, or both, of at least one blade of the plurality of blades, wherein the one or more turbulators comprise a rib coupled to the suction face of the at least one blade, wherein the at least one blade comprises a first through-opening extending between the suction face and the pressure face, wherein the rib comprises a second through-opening, and wherein the rib is coupled to the suction face with the second through-opening aligned with the first through-opening.

2. The impeller of claim 1, wherein the impeller is a radial impeller, the radial impeller including a Rushton impeller.

3. The impeller of claim 1, wherein the rib is inclined at an angle in a range from about 30 degrees to about 150 degrees relative to a radial axis of the hub.

4. The impeller of claim 1, wherein the one or more turbulators further comprise a corrugated surface or a flat and smooth surface.

5. The impeller of claim 1, wherein the one or more turbulators further comprise a dimple.

6. The impeller of claim 1, wherein the one or more turbulators further comprise a protrusion.

7. The impeller of claim 1, wherein the one or more turbulators further comprise a dimple, a protrusion, and a groove.

8. The impeller of claim 1, wherein the one or more turbulators comprise an array of ribs, an array of dimples, an array of through-openings, an array of protrusions, or combinations thereof.

9. The impeller of claim 1, wherein the one or more turbulators are disposed proximate to a tip edge of the at least one blade of the plurality of blades.

10. The impeller of claim 1, wherein the one or more turbulators are disposed on the plurality of blades.

11. A bioreactor sub-system, comprising:
a culture vessel used for culturing a plurality of cells dispersed in a cell-culture media; and
at least one impeller disposed within the culture vessel and configured to stir the cell-culture media and the plurality of cells; wherein the at least one impeller comprises:
a hub;
a plurality of blades disposed along a circumferential direction of the hub and spaced apart from each other, wherein each of the plurality of blades is coupled to at least a portion of a circumference and/or a top surface of the hub, wherein each blade of the plurality of blades comprises a pressure face and a suction face; and
one or more turbulators disposed on at least a portion of the suction face, the pressure face, or both, of at least one blade of the plurality of blades, wherein the one or more turbulators comprise a rib coupled to the suction face of the at least one blade, wherein the at least one blade comprises a first through-opening extending between the suction face and the pressure face, wherein the rib comprises a second through-opening, and wherein the rib is coupled to the suction face with the second through-opening aligned with the first through-opening.

12. The bioreactor sub-system of claim 11, wherein the impeller is a radial impeller, the radial impeller including a Rushton impeller.

13. The bioreactor sub-system of claim 11, wherein the one or more turbulators further comprise a dimple, a protrusion, a groove, or combinations thereof.

14. A bioreactor system, comprising:
a culture vessel used for culturing a plurality of cells dispersed in a cell-culture media;
a heating assembly coupled to the culture vessel for maintaining the cell-culture media at a predetermined temperature;
a sparger operatively coupled to the culture vessel and configured to inject air into the culture vessel; and at least one impeller disposed in the culture vessel and configured to stir the cell-culture media and the plurality of cells; wherein the at least one impeller comprises:

a hub;

a plurality of blades disposed along a circumferential direction of the hub and spaced apart from each other, wherein each of the plurality of blades is coupled to at least a portion of a circumference and/or a top surface of the hub, wherein each blade of the plurality of blades comprises a pressure face and a suction face; and one or more turbulators disposed on at least a portion of the suction face, the pressure face, or both, of at least one blade of the plurality of blades, wherein the one or more turbulators comprise a rib coupled to the suction face of the at least one blade, wherein the at least one blade comprises a first through-opening extending between the suction face and the pressure face, wherein the rib comprises a second through-opening, and wherein the rib is coupled to the suction face with the second through-opening aligned with the first through-opening.

15. The bioreactor system of claim 14, wherein the impeller is a radial impeller, the radial impeller including a Rushton impeller.

16. The bioreactor system of claim 14, wherein the one or more turbulators further comprise a dimple, a protrusion, a groove, or combinations thereof.

17. The bioreactor system of claim 14, further comprising a drive unit operatively coupled to the at least one impeller via the hub and a shaft.

* * * * *